(12) United States Patent
Trinkle et al.

(10) Patent No.: US 9,012,235 B2
(45) Date of Patent: Apr. 21, 2015

(54) MULTI-SAMPLE PARTICLE ANALYZER AND METHOD FOR HIGH THROUGHPUT SCREENING

(75) Inventors: Linda Trinkle, Albuquerque, NM (US); R. Terry Dunlay, Albuquerque, NM (US); Bruce Edwards, Albuquerque, NM (US); Larry Sklar, Albuquerque, NM (US)

(73) Assignee: IntelliCyt Corporation, Albuquerque, NM (US)

(*) Notice: Subject to any disclaimer, the term of this patent is extended or adjusted under 35 U.S.C. 154(b) by 0 days.

(21) Appl. No.: 13/588,984

(22) Filed: Aug. 17, 2012

(65) Prior Publication Data

US 2012/0309635 A1    Dec. 6, 2012

Related U.S. Application Data

(62) Division of application No. 12/679,448, filed as application No. PCT/US2009/041680 on Apr. 24, 2009, now abandoned.

(60) Provisional application No. 61/080,171, filed on Jul. 11, 2008.

(51) Int. Cl.
*G01N 35/08* (2006.01)
*G01N 35/10* (2006.01)

(52) U.S. Cl.
CPC ............ *G01N 35/08* (2013.01); *G01N 35/1067* (2013.01); *G01N 35/1074* (2013.01); *G01N 35/1095* (2013.01)

(58) Field of Classification Search
USPC .......... 435/7.1, 7.2, 286.5, 286.6, 287.1, 435/287.3, 287.8, 288.4; 436/52, 53, 54, 436/10, 65, 172, 180; 422/50, 63, 65, 68.1, 422/81, 82.05, 82.08, 521–524
See application file for complete search history.

(56) References Cited

U.S. PATENT DOCUMENTS

| | | | | |
|---|---|---|---|---|
| 4,116,631 A | * | 9/1978 | Trinel et al. | 436/53 |
| 4,853,336 A | * | 8/1989 | Saros et al. | 436/53 |
| 5,565,353 A | * | 10/1996 | Klebe et al. | 435/383 |
| 5,788,927 A | * | 8/1998 | Farrell et al. | 422/63 |
| 6,132,685 A | * | 10/2000 | Kercso et al. | 422/566 |
| 6,150,180 A | * | 11/2000 | Parce et al. | 506/7 |
| 6,159,739 A | * | 12/2000 | Weigl et al. | 436/52 |
| 6,727,071 B1 | * | 4/2004 | Dunlay et al. | 435/7.21 |
| 6,878,556 B2 | * | 4/2005 | Sklar et al. | 435/286.5 |
| 6,890,487 B1 | * | 5/2005 | Sklar et al. | 422/93 |
| 7,758,811 B2 | * | 7/2010 | Durack et al. | 422/73 |
| 8,021,872 B2 | * | 9/2011 | Sklar et al. | 435/287.3 |
| 2011/0312536 A1 | * | 12/2011 | Sklar et al. | 506/12 |
| 2012/0061584 A1 | * | 3/2012 | Trinkle et al. | 250/428 |

* cited by examiner

*Primary Examiner* — Gail R Gabel
(74) *Attorney, Agent, or Firm* — Peacock Myers, P.C.; Janeen Vilven

(57) ABSTRACT

Embodiments of the present invention provide a system and method for analyzing a plurality of samples comprising obtaining with an autosampler a plurality of samples from a first plate having a plurality of sample wells wherein the autosampler has a plurality of probes for sampling a set of samples and wherein each probe of the plurality of probes is in communication with a separate flow cytometer via a separate conduit. The plurality of samples comprising particles is moved into a fluid flow stream for each separate conduit. Adjacent ones of the plurality of samples are separated from each other in the fluid flow stream by a separation gas, thereby forming a gas-separated fluid flow stream. The gas-separated fluid flow stream is independently guided to and through each separate flow cytometer.

19 Claims, 15 Drawing Sheets

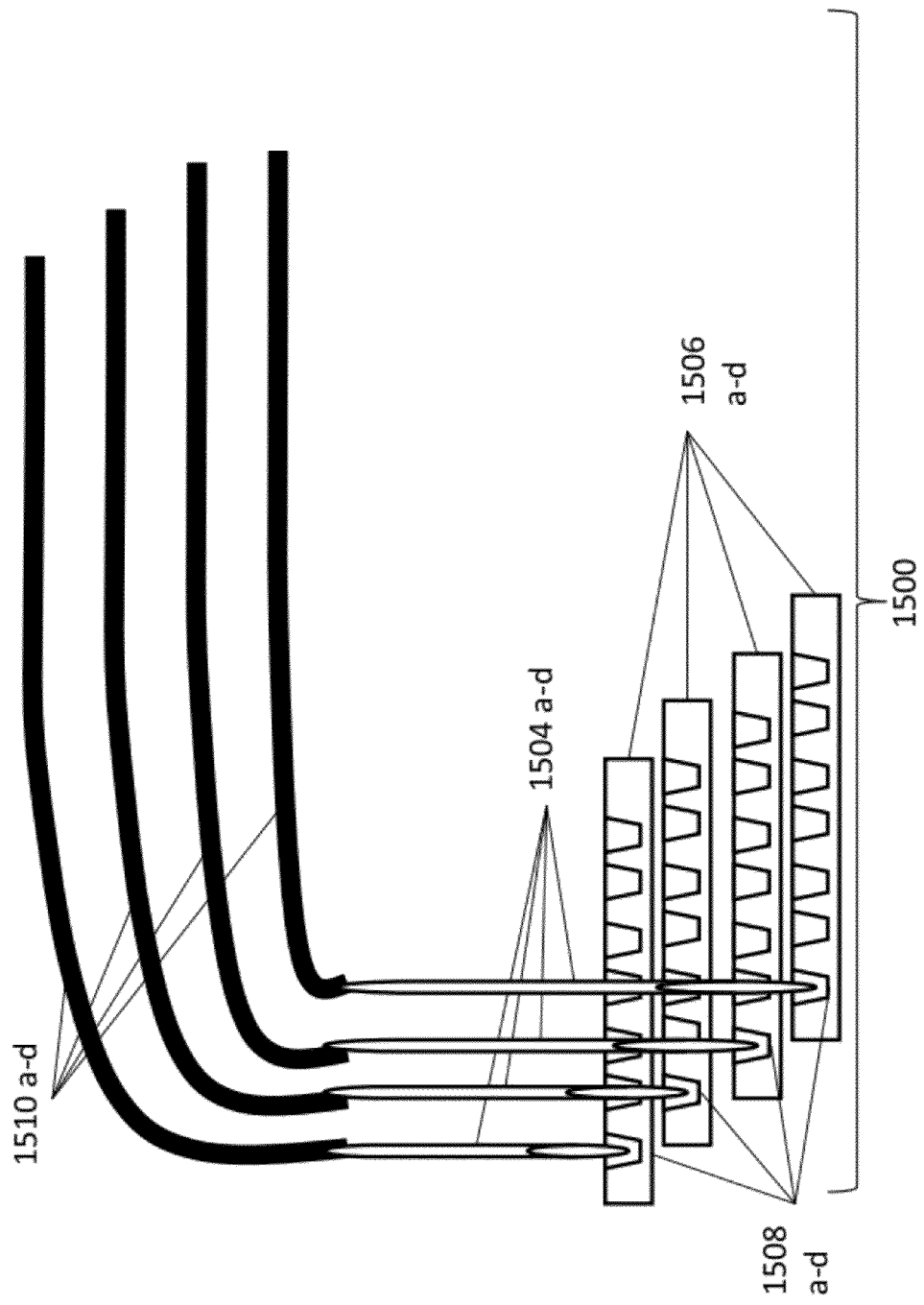

MULTI-SAMPLE PARTICLE ANALYZER AND METHOD FOR HIGH THROUGHPUT SCREENING

CROSS-REFERENCE TO RELATED APPLICATIONS

This application is a divisional application of the filing of U.S. patent application Ser. No. 12/679,448, entitled "Multi-Sample Particle Analyzer System and Method for High-Throughput Screening", filed on Mar. 22, 2010, which is a National Stage of International Application Serial No. PCT/US09/41680, entitled "Multi-Sample Particle Analyzer System and Method for High-Throughput Screening", filed on Apr. 24, 2009, which claims priority to and the benefit of the filing of U.S. Provisional Patent Application Ser. No. 61/080,171, entitled "Multi-Sample Particle Analyzer System and Method for High-Throughput Screening", filed on Jul. 11, 2008, and the specification and claims thereof are incorporated herein by reference.

BACKGROUND OF THE INVENTION

1. Field of the Invention (Technical Field)

The present invention relates to a particle analyzer and sample handling for use with particle analysis apparatus and a method for high-throughput analysis using the same.

Particle analysis using flow cytometry is used to characterize cells and particles by making measurements on each at rates up to thousands of events per second. The measurement consists of simultaneous detection of the light scatter and fluorescence associated with each event. Commonly, the fluorescence characterizes the expression of cell surface molecules or intracellular markers sensitive to cellular responses to drug molecules. The technique often permits homogeneous analysis such that cell associated fluorescence can often be measured in a background of free fluorescent indicator. The technique often permits individual particles to be sorted from one another.

However, a deficiency with conventional flow cytometry is that it does not allow for the analysis of multiple samples consisting of multiple cells or particles in a rapid manner, a fact that has limited the uses of flow cytometry in drug discovery and other high throughput screening applications. For example, the industrial standard for high throughput drug discovery is 100,000 samples per day. Because of its low throughput, flow cytometry has generally not been considered applicable to high throughput screening applications in areas such as drug discovery, antibody hybridoma screening, and systems biology.

There have been several efforts at automated sample handling in flow cytometry. For example, sample handling systems are known that use carousels to handle samples from standard sized tubes and sample injection systems which handle samples from 96-384 well microplates. These systems treat each tube or well as a single sample. A separate data file is created for each sample. These systems typically intake samples at a rate of approximately 1 up to 5 samples per minute and require priming the sample line with each individual specimen before analysis. Therefore, a single data file exists for each well sample interrogated.

Other groups have also used valves and syringes in flow cytometry, most notably, the "flow injection" group, Lindberg et al. at University of Washington. However, the processes described above did not address throughput speed. A group at the University of New Mexico has used high throughput flow cytometry and achieved sampling rates as high as 40 samples per minute, see U.S. Pat. Nos. 6,878,556, 6,890,487, 7,368,084, the entire disclosure and contents of which is hereby incorporated by reference. However, to our knowledge, no one has reported the capability to process samples at rates higher than 40 samples per minute for flow cytometry.

The presence of uncontrolled bubbles in the flow cytometer system is one of the primary sources of corrupted experimental data. Flow cytometers may periodically experience bubbles in the sheath fluid or sample fluid lines. Precautions are taken to exclude bubbles as bubbles are known to cause anomalies in the flow within the flow cytometer system that reduce the performance of the flow cytometer. Furthermore, bubbles passing through the interrogation zone of the flow cytometer can cause spurious or false event signals that corrupt the experimental data being collected. The user can take corrective action only after the bubbles have been detected, which often occurs after experimental data has been corrupted and the user has been inconvenienced. Therefore the flow cytometry art teaches against introduction of bubbles in the flow stream.

SUMMARY OF THE INVENTION

It is an aspect of the present invention to provide a flow cytometry apparatus that meets the needs of high throughput screening for multiwell, for example, 96, 384, or 1536 well microplates.

It is an aspect of the present invention to provide a method for analyzing a plurality of samples in a single source file using high throughput screening.

It is another aspect of the present invention to separate with a gas a plurality of adjacent samples in a fluid flow stream which passes through a flow cytometer for analysis.

One embodiment of the present invention provides for a method for analyzing a plurality of samples comprising obtaining with an autoampler a plurality of samples from a first plate having a plurality of sample wells wherein the autosampler has a plurality of probes for sampling a set of samples and wherein each probe of the plurality of probes is in communication with a separate flow cytometer via a separate conduit. The plurality of samples comprising particles is moved into a fluid flow stream for each separate conduit. Adjacent ones of the plurality of samples are separated from each other in the fluid flow stream by a separation gas, thereby forming a gas-separated fluid flow stream. The gas-separated fluid flow stream is independently guided to and through each separate flow cytometer.

Another embodiment of the present invention provides for a method for analyzing a plurality of samples comprising the steps of obtaining with an autosampler a plurality of samples from a first plate having a plurality of sample wells wherein the autosampler has a plurality of probes for sampling a set of samples and wherein each probe of the plurality of probes is in communication with a single multi-channel flow cytometer via a separate conduit attached to each of the probes in the plurality of probes. The plurality of samples comprising particles are moved into a fluid flow stream for each separate conduit. Adjacent ones of the plurality of samples are separated from each other in the fluid flow stream by a separation gas, thereby forming a gas-separated fluid flow stream. The gas separated fluid flow stream is independently guided to and through the single multi-channel flow cytometer. The multi-channel flow cytometer is operated to focus the gas-separated fluid flow stream and to selectively analyze the particles in each of the plurality of samples as the gas-separated fluid flow stream passes through the multi-channel flow cytometer.

In a preferred embodiment, the step of moving may occur with gravity, or suction, or pumping or pushing. In another preferred embodiment, moving the plurality of samples is with a fluid moving device located before or after the cytometer. For example the fluid moving device is a multihead peristaltic pump. The conduit through which the fluid flow streams move may be tubing. The step of moving the plurality of fluid flow streams through each separate conduit is at a rate that may be independently controlled for each conduit.

In another preferred embodiment the first plate is positioned on a platform that is moveable in the xyz direction to bring the samples to the probes. Alternatively the plurality of probes are positionable and move to the samples on the first plate. In another embodiment a probe of the plurality of probes is positionable and moves to a plurality of samples located on a second plate. Further still, two or more probes may or may not occupy the same sample well at the same time.

Yet another embodiment to the present invention provides for a flow cytometry apparatus comprising an autosampler comprising a plurality of probes with each probe suitable for inserting a plurality of samples comprising particles from a plurality of respective source wells into a separate fluid flow stream. A plurality of flow cytometers in communication with the plurality of probes of the autosampler via a separate conduit connecting one probe of the plurality of probes with one flow cytometer of the plurality of flow cytometers. Moving the plurality of samples in each separate fluid flow streams through each separate conduit to a selected cytometer of the plurality of flow cytometers, the plurality of probes introducing aliquots of a separation fluid between successive ones of the plurality of samples in each of the separate fluid flow streams to configure each of the separate fluid flow streams as a gas-separated fluid flow stream, each of the plurality of flow cytometers focusing the gas-separated fluid flow stream delivered by the separate conduit and selectively analyzing the particles in each of the plurality of samples as the gas-separated fluid flow stream passes through each separate cytometer of the plurality of cytometers. In a preferred embodiment of the present invention the plurality of probes are positioned on a bracket. Alternatively, the plurality of probes are positionable relative to the plurality of respective source wells and/or the bracket is fixed relative to the plurality of respective source wells and/or the probes are independently positionable relative to each other and the plurality of respective source wells. In a preferred embodiment, the apparatus further comprises a fluid movement device which may be a pump such as a peristaltic pump. The pump may be positioned before or after each flow cytometer. The fluid movement device comprises a plurality of fluid movement devices each one of the plurality of fluid movement devices may be associated with a separate conduit. In a preferred embodiment the step of moving is selected from pumping, pushing, suctioning or moving with gravity.

Yet another embodiment provides for a flow cytometry apparatus comprising an autosampler comprising a plurality of probes for inserting a plurality of samples comprising particles from a plurality of respective source wells into a plurality of fluid flow streams. A multi-channel flow cytometer is in communication with the plurality of probes of the autosampler via a plurality of separate conduits connected to one each of the probes of the plurality of probes wherein each of the separate conduits of the plurality moves a separate fluid flow stream of the plurality of fluid flow streams. The plurality of samples moving in each of the separate fluid flow streams moving in each separate conduit moves to the multi-channel flow cytometer with the autosampler introducing aliquots of a separation fluid between successive ones of the plurality of samples in the fluid flow stream to configure the fluid flow stream as a gas-separated fluid flow stream. The multi-channel flow cytometer focusing the gas-separated fluid flow stream delivered by the conduit from the autosampler and selectively analyzing the particles in each of the plurality of samples as the gas-separated fluid flow stream passes through the multi-channel flow cytometer.

Yet another embodiment to the present invention provides for a flow cytometry apparatus comprising an autosampler comprising a probe with each probe suitable for inserting a sample comprising particles from a source well into a fluid flow stream. A flow cytometer in communication with the probe of the autosampler via a conduit connecting the probe with the flow cytometer. Moving the samples in the fluid flow stream through the conduit to the cytometer, the probe introducing aliquots of a separation fluid between successive ones of the plurality of samples in the fluid flow streams to configure the fluid flow stream as a gas-separated fluid flow stream, each of the plurality of flow cytometers focusing the gas-separated fluid flow stream delivered by the separate conduit and selectively analyzing the particles in each of the plurality of samples as the gas-separated fluid flow stream passes through the flow cytometer. The apparatus further comprising a fluid movement device located after the cytometer such that the fluid movement device assists the autosampler with introducing aliquots of a separation fluid between successive ones of the plurality of samples. In an alternative embodiment the gas is pushed into the sample via pressurization.

Additional objects and advantages of the present invention will be apparent in the following detailed description read in conjunction with the accompanying drawing figures.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 15 illustrates a particle analysis apparatus according to another embodiment of the present invention.

DETAILED DESCRIPTION OF THE INVENTION

Figure 1:
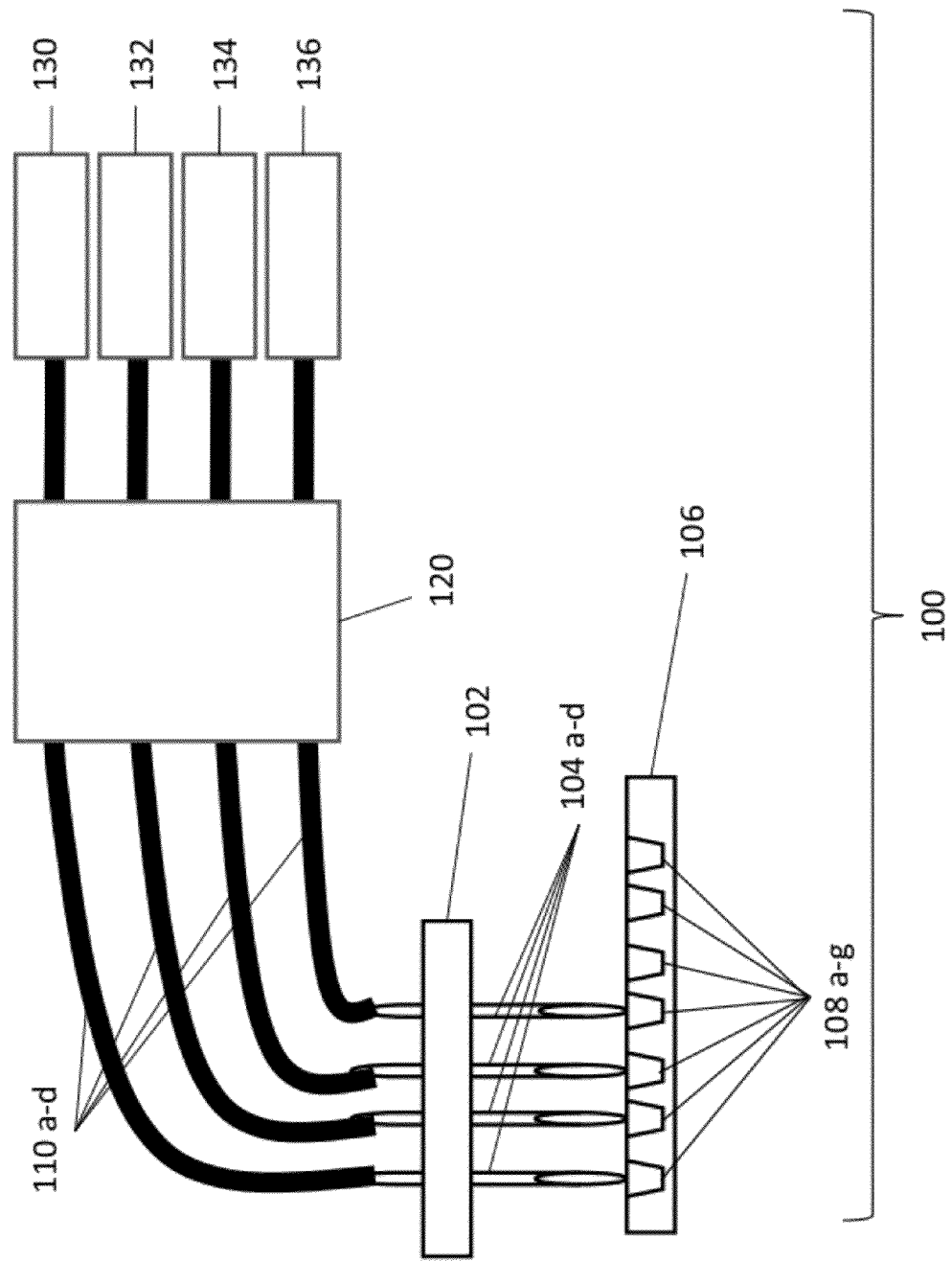
FIG. 1 illustrates a particle analysis apparatus according to one embodiment of the present invention.

It is advantageous to define several terms before describing the invention. It should be appreciated that the following definitions are used throughout this application.
Definitions:

Where the definition of terms departs from the commonly used meaning of the term, applicant intends to utilize the definitions provided below, unless specifically indicated.

For the purposes of the present invention, the term "particles" refers to any particles that may be detected using a particle analyzer such as a cytometer where particles are focused hydrodynamically, acoustically or with capillary action.

For the purposes of the present invention, the term "source well" refers to any container that is intended to hold a fluid such as a fluid sample, for example a well on a well plate, whether or not the source well contains a sample. For the purposes of the present invention, the term "sample source well" refers to a source well containing a sample.

For the purposes of the present invention, the term "sample" refers to a fluid solution or suspension containing particles to be analyzed using a method and/or apparatus of the present invention. The particles to be analyzed in a sample may be tagged, such as with a fluorescent tag. The particles to be analyzed may also be bound to a bead, a receptor, or other useful protein or polypeptide, or may just be present as free particles, such as particles found naturally in a cell lysate, purified particles from a cell lysate, particles from a tissue culture, etc. The sample may include chemicals, either organic or inorganic, used to produce a reaction with the particles to be analyzed. When the particles to be analyzed are biomaterials, drugs may be added to the samples to cause a reaction or response in the biomaterial particles. The chemicals, drugs or other additives may be added to and mixed with the samples when the samples are in sample source wells or the chemicals, drugs or other additives may be added to the samples in the fluid flow stream after the samples have been intaken by the autosampler.

For the purposes of the present invention, the term "adjacent samples" refers to two samples in a fluid flow stream that are separated from each other by a separation gas, such as an air bubble. For the purposes of the present invention, the term "immediately adjacent samples" refers to adjacent samples that are only separated from each other by a separation gas. For the purposes of the present invention, "buffer fluid separated adjacent samples" refers to adjacent samples that are separated from each other by two separation gas bubbles and a buffer fluid, with the buffer fluid being located between the two separation gas bubbles.

For the purposes of the present invention, the term "separation gas" refers to any gas such as air, an inert gas, or fluid, etc. that can be used to form a gas bubble or immiscible fluid between adjacent samples or between a sample and a buffer fluid. An immiscible fluid is a fluid that will not substantially mix with and contaminate a sample.

For the purposes of the present invention, the term "buffer fluid" refers to a fluid that is substantially free of the particles to be detected by the apparatus and method of the present invention.

For the purposes of the present invention, the term "plurality" refers to two or more of anything, such as a plurality of samples. For the purposes of the present invention, the terms "a", "an" or "the" refers to one or more of anything, such as a sample or the sample.

For the purposes of the present invention, the term "homogeneous" refers to a plurality of identical samples. The term "homogeneous" also refers to a plurality of samples that are indistinguishable with respect to a particular property being measured by an apparatus or a method of the present invention.

For the purposes of the present invention, the term "heterogeneous" refers to a plurality of samples in a fluid flow stream in which there are at least two different types of samples in the fluid flow stream. One way a heterogeneous plurality of samples in a fluid flow stream of the present invention may be obtained is by intaking different samples from different source wells in a well plate. The identification of sequential samples to be analyzed in the fluid flow stream is based upon the separation of the fluid samples by one or more bubbles of a separation gas and/or one or more portions of a buffer fluid. Another way of obtaining a heterogeneous plurality of samples is by intaking different samples from identical source wells at various time points where a reaction or a series of reactions is or had been occurring.

For the purposes of the present invention, the term "fluid flow stream" refers to a stream of fluid samples, separated by one or more bubbles of a separation gas and/or one or more portions of a buffer fluid.

For the purpose of the present invention, the term "fluid flow path" refers to device such as a conduit, tube, channel, etc. through which a fluid flow stream flows. A fluid flow path may be composed of several separate devices, such as a number of connected or joined pieces of tubing or a single piece of tubing, alone or in combination with channels or other different devices.

For the purposes of the present invention, the term "high speed multi-sample tube" includes any tube that may be used with a fluid movement device such as a peristaltic pump, a syringe pump, an injector, or gravity. The tubing for use with a peristaltic pump for example may have compression characteristics that allow a peristaltic pump to move samples separated by a separation gas through the tube at a speed of at least 6 samples per minute without causing adjacent samples to mix with each other.

DETAILED DESCRIPTION OF THE INVENTION

An embodiment of the present invention preferably uses a separation fluid, such as air, water, bubbles, or a combination thereof to separate samples introduced from an autosampler into a conduit such as a tubing line that connects directly or indirectly the autosampler and a particle analyzer such as a flow cytometer using sheath fluid or acoustic forces or capillary action to focus particles to an interrogation zone of a flow cell. In one embodiment, the fluid is moved from the autosampler to the particle analyzer. The fluid sample is pulled or pushed through a conduit by for example by pump action, suction, syringe or by gravity. A separation fluid such as a gas, preferably air bubbles, effectively separates a sample into a plurality of samples or separates a first sample from a second sample which have previously occupied different sample source well locations on a plate. Samples separated by air bubbles are analyzed by the particle analyzer as a continuous fluid sample. Data from the optical signature of a plurality of samples in the fluid sample stream is collected in a single data file. An interrogation zone is an area within a particle analyzer where the particles are aligned or focused. A light source such as a laser and a light detector are connected to the interrogation zone such that a sample flowing through the interrogation zone can be optically analyzed through methods known in the art of flow cytometry. The particle analyzer may or may not contain a flow cell.

FIG. 1 illustrates a preferred multi-sample particle analyzer apparatus 100 of one embodiment of the present invention. Multi-sample particle analyzer apparatus 100 preferably comprises conventional autosampler, for example a gantry robot, having adjustable XYZ positioning arm 102 on which is positioned a plurality of hollow probes 104a-d. As arm 102 moves back and forth (left and right in FIG. 1) and side to side (into and out of the plane of FIG. 1), one or more of a plurality of probes selected from 104a-d are lowered into different individual source wells 108a-g of plate 106 to obtain a first sample. The movement of the sample probes with regards to the sample source wells is programmed by a user into a computer programmed with instructions for moving the arm in the XYZ directions in space. The first sample may have been spiked with particles of different size or tags having a fluorescent property that will be detected upon interrogation of the sample with a light source such as a laser. One or more of probes 104a-d uptakes a sample from a separate well 108a-d.

Once a sample is picked up by one or more of the plurality of probes 104a-d, the sample is moved through a tube 110a-d in communication with the corresponding probe selected from 104a-d such that the tube extends from autosampler XYZ arm 102 and into a multi-channel fluid movement device such as a multihead peristaltic pump or multiple injectors 120 and then into a particle analyzer 130, 132, 134, 136 in communication with the respective tube 110a-d. A particle analyzer 130, 132, 134, 136 may comprise one or more of the following: a flow cell, a means for focusing the particles to a desired location within the flow cell for the sample to be analyzed, a laser interrogation device, an optical system configured to receive and focus the light from a laser source, a spectrum detector, a fiber optic transmission means, processor for collecting data from particles, and data storage. A laser interrogation device examines individual samples flowing through a flow cell located therein at a laser interrogation point. In between intaking sample material from each of source wells 108, one or more of the plurality of probes 104a-d is allowed to intake a fluid such as air, thereby forming a gas separation between each adjacent sample. The continuous fluid flow stream from each of the probes 104a-d and through the respective tube 110a-d are communicated to a respective individual particle analyzer for example 130, 132, 134, 136. In a preferred embodiment the fluid movement device is positioned after the particle analyzer and therefore the sample moves from the sample probe to the particle analyzer through the tube.

When a fluid sample having particles therein passes through a laser interrogation point, the particles in the fluid sample are sensed by the particle analyzer for example 130 of FIG. 1 due to, for example, a fluorescent tag on the particles or the light scattering properties of the particles themselves. In contrast, when air bubbles pass through laser interrogation point no particles are sensed. Therefore, a graph of the data points of fluorescence sensed versus time for a series of samples analyzed using the particle analyzer of the present invention will form distinct groups, each aligned with the time that a sample containing particles passes through the laser interrogation point.

In order to detect the presence of each of two or more different types of samples, in a heterogeneous plurality of samples, each of the two or more different types of samples may be tagged with different fluorescent tags, different amounts of a single tag or some combination of different tags and different amount of a single tag. In such a case, the groupings of data points will vary vertically on a fluorescence versus time graph, depending on which type of sample is being sensed. As with the case of sensing a single type of sample, each sensed sample will exhibit a group of data points aligned with the time that the sample passes through the laser interrogation point.

In one embodiment of the device, samples from selected wells in the well plate are introduced as a single specimen to a particle analyzer and data from all of the wells in the plate or a portion of a plate are collected in a single data file by the particle analyzer system. In a preferred embodiment, sample from every well having sample herein in the plate is introduced as a single specimen in a continuous manner. In the case of multiprobe sample introduction, multiple analyzers may create multiple data files that the analysis protocol will associate with the well from which the sample was taken. Multichannel sampling from a single plate into multiple particle analyzers, or multiplate data from multiple analyzers are analyzed by proprietary software that correlates the data with individual well information.

In an alternative embodiment of the present invention using the particle analyzer apparatus of FIG. 1, some of the source wells on the well plate of the apparatus illustrated in FIG. 1 may contain a buffer solution to allow for the formation of buffer fluid separated adjacent samples in a tube through which samples pass. When this is the case, after the first sample is taken up by the probe from a first well, the probe intakes air, then buffer solution, located in second well, then the probe uptakes air again, and then the probe uptakes a second sample, located in a third well. This sequence may then be repeated for additional samples located in subsequent wells, which the probe subsequently intakes.

Figure 14:
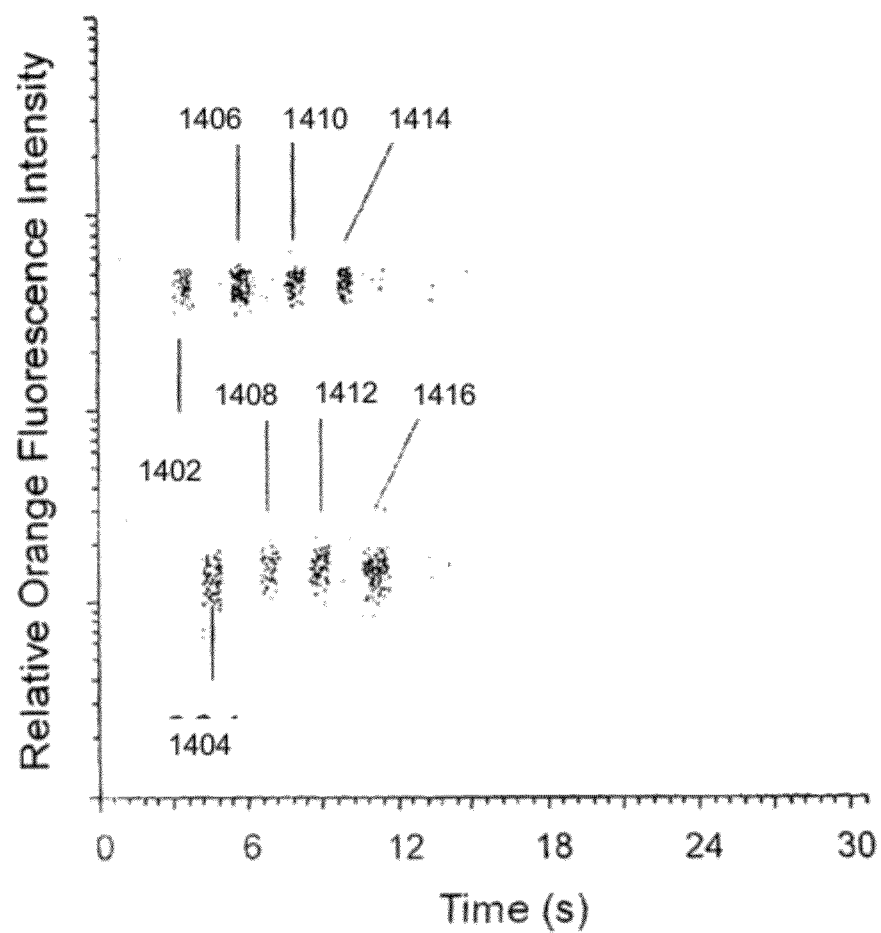
FIG. 14 illustrates cytometry results of fluorescence vs. time with a system and method according to one embodiment of the present invention.

A graph of the data points of fluorescence detected versus time for a series of samples analyzed using one embodiment of the particle analyzer of the present invention will form distinct groups, each aligned with the time that a sample containing particles passes through the laser interrogation point (see for example FIG. 14). In order to detect the presence of two or more different types of samples, each of the two or more different types of samples may be tagged with different fluorescence tags or different amounts of a single tag as compared to the particle in the sample. In such a case, the groupings of data points will vary vertically on a fluorescence versus time graph, depending on which type of sample is being sensed. As with the case of sensing a single type of sample, each sensed sample will exhibit a group of data points aligned with the time that the sample passes through the laser interrogation point.

Alternatively, buffer fluid separated adjacent samples may be formed by providing a reservoir of buffer fluid in the autosampler or attached to the autosampler to inject buffer fluid into the tube for the fluid flow stream. In this case, after each sample is taken up by the probe, the probe intakes air, then buffer fluid is injected into the tube for the fluid flow stream, then the probe intakes air again, and then the probe intakes a second sample. This sequence may then be repeated for subsequent samples to be separated by a buffer fluid.

One embodiment of the present invention is compatible with standard commercial multi-well plates for use with autosamplers from 96 well plates to 1536 well plates or greater. The source wells of one embodiment of the present invention may be all filled with samples and/or buffer fluids, or some may be left empty or some combination thereof. When there is a plurality of different types of samples in the source wells of a well plate, the sample types may be arranged in the order in which they are taken up by the probe, or the sample types may be arranged in any other convenient arrangement. For example, all of the source wells in a first row of source wells may contain one sample type and all of the source wells of a second row may contain a second sample type. Or individual wells may contain multiple specimens that are differentiated by size of particles within the sample or fluorescent probes within the sample associated with particles therein.

Figure 2:
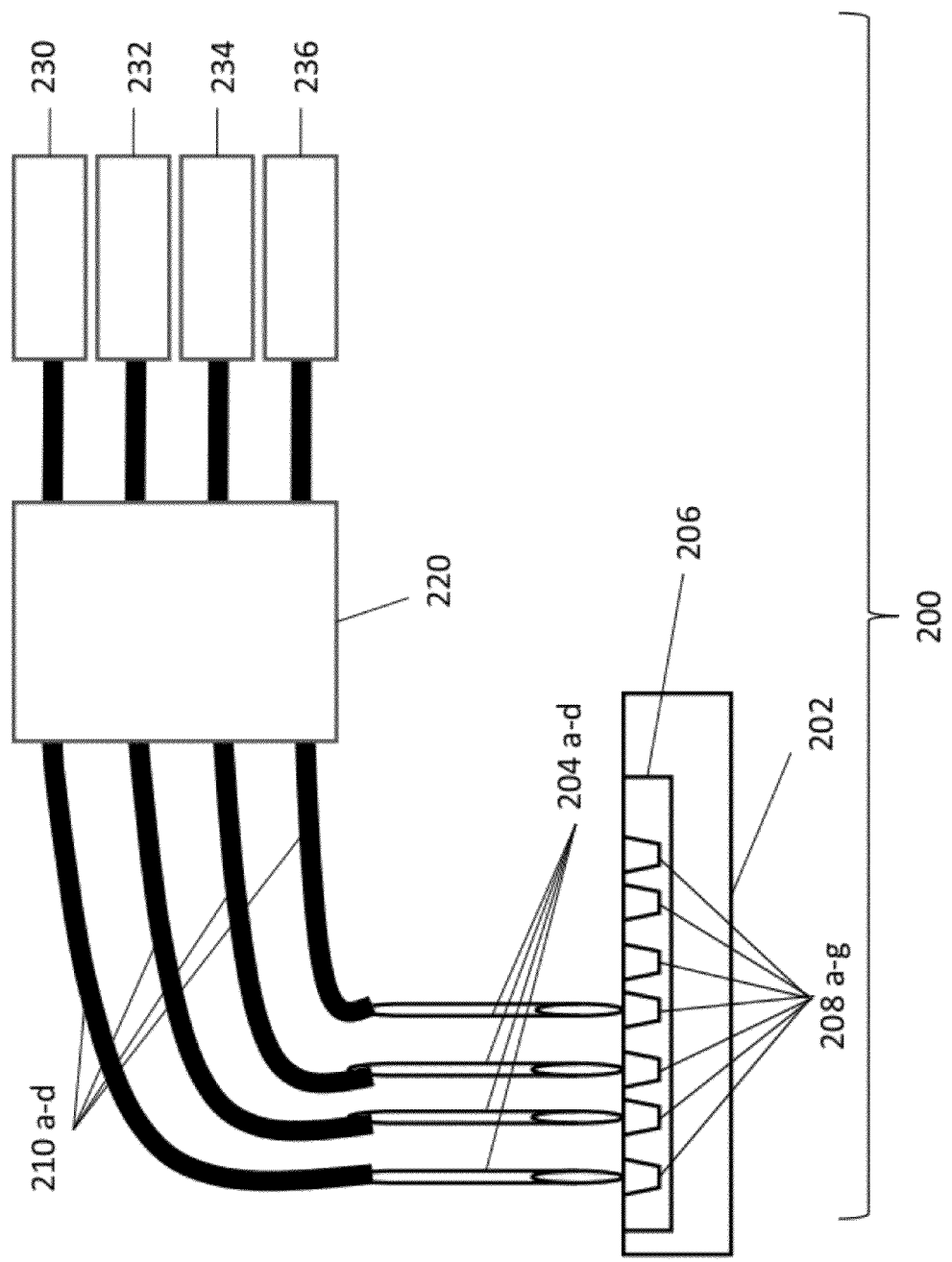
FIG. 2 illustrates a particle analysis apparatus according to another embodiment of the present invention.

The source wells may be of any conventional shape used for source wells in a well plate for an autosampler. Preferably, when small amounts of sample are used in each source well, the source wells are conical in shape, to allow even the smallest amounts of sample to be withdrawn by the probe or to allow the particles to concentrate in the bottom of the well. The use of a well plate with conical source wells reduces the problems associated with the settling of particles to the bottom of the well prior to being intaken by the probe. A device which resuspends the particles before and during sampling such as an orbital shaker can be used to reduce issues associated with settling of particles and is being used in the current embodiment of the invention. FIG. 2 illustrates an alternative embodiment of the multi-sample particle analyzer apparatus 200 of the present invention. Multi-sample particle analyzer apparatus 200 preferably comprises conventional XYZ stage 202 on which is positioned a well plate 206. The plurality of probes 204a-d are stationary as stage 202 moves back and forth (left and right in FIG. 2) and side to side (into and out of the plane of FIG. 2), the stage 202 raises and lowers the well plate 206 to a plurality of probes 204a-d so that individual samples from individual source wells 208a-g are obtained from well plate 206. Alternatively, the probes may be positionable and move to the sample well. Further still, the probes and the well plate may move with respect to each other in a coordinated fashion.

Once a sample is picked up by one or more of the plurality of probes 204a-d, the sample is moved through a tube 210a-d in communication with the corresponding probe selected from 204a-d such that the tube extends from the respective probe 204a-d into a multi-channel fluid movement device 220 and then into the particle analyzers in communication with the respective tube 210a-d. However, the fluid movement device 220 is not required to be located between the sample probe and the particle analyzer as the fluid movement device may be located after the particle analyzer or may be absent altogether in the case of gravity moving the samples. A particle analyzer 230, 232, 234, 236 comprises a flow cell and a laser interrogation device. A laser interrogation device examines individual samples flowing through a flow cell located therein at a laser interrogation point. In between taking up sample material from each of source wells 208a-d for example, one or more of the plurality of probes 204a-d is allowed to intake (sometimes referred to herein as uptake) a fluid such as air prior to moving to a subsequent well, thereby forming a gas separation between each adjacent sample. The continuous fluid flow stream from each of the probes 204a-d and through the respective tube 210a-d are communicated to a respective individual particle analyzer 230, 232, 234, 236.

Multichannel fluid movement device may be for example a multihead peristaltic pump or a multichannel push-pull syringe system.

Figure 3:
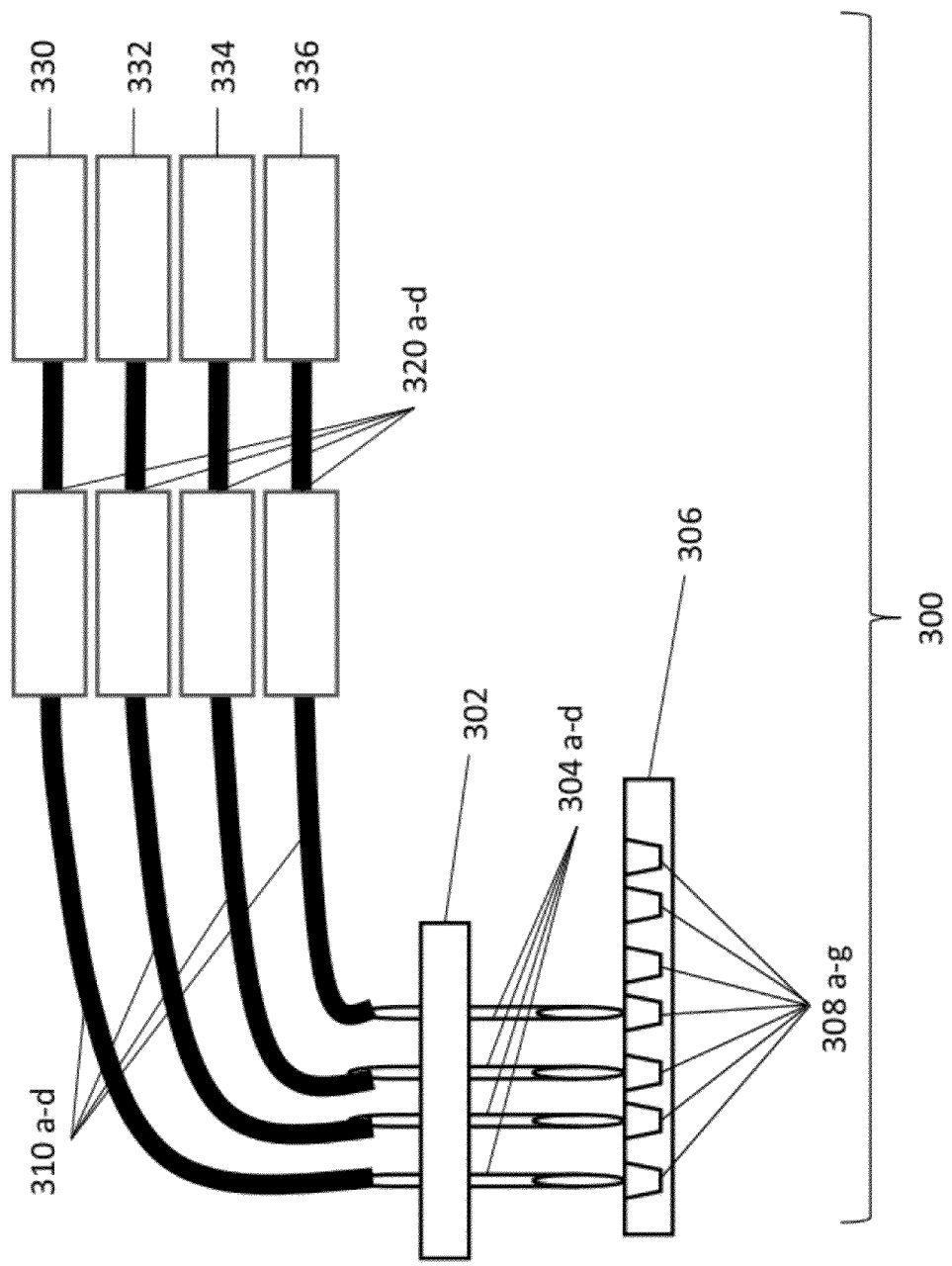
FIG. 3 illustrates a particle analysis apparatus according to another embodiment of the present invention.

FIG. 3 illustrates an alternative embodiment of the multi-sample particle analyzer apparatus 300 of the present invention. Multi-sample particle analyzer apparatus 300 preferably comprises conventional autosampler having adjustable XYZ positioning arm 302 on which is positioned a plurality of hollow probes 304a-d. As arm 302 moves back and forth (left and right in FIG. 3) and side to side (into and out of the plane of FIG. 3), a plurality of probes selected from 304a-d are lowered into individual source wells 308 of well plate 306 to obtain a sample.

Once a sample is picked up by one or more of the plurality of probes 304a-d, the sample is moved through a conduit 310a-d in communication with the corresponding probe selected from 304a-d such that the conduit extends from autosampler XYZ arm 302 to the particle analyzers in communication with the respective tube 310a-d. A particle analyzer 330, 332, 334, 336 comprises a flow cell and a laser interrogation device. A laser interrogation device examines individual samples flowing through a flow cell located therein at a laser interrogation point. In between intaking sample material from each of source wells 308, one or more of the plurality of probes 304a-d is allowed to intake a fluid such as air, thereby forming a gas separation between each adjacent sample. The continuous fluid flow stream from each of the probes 304a-d and through the respective tube 310a-d are communicated to a respective individual particle analyzer 330, 332, 334, 336. The sample is moved to a particle analyzer by a fluid movement device which may be located before the probe, between the probe and the particle analyzer or after the particle analyzer.

Figure 4:
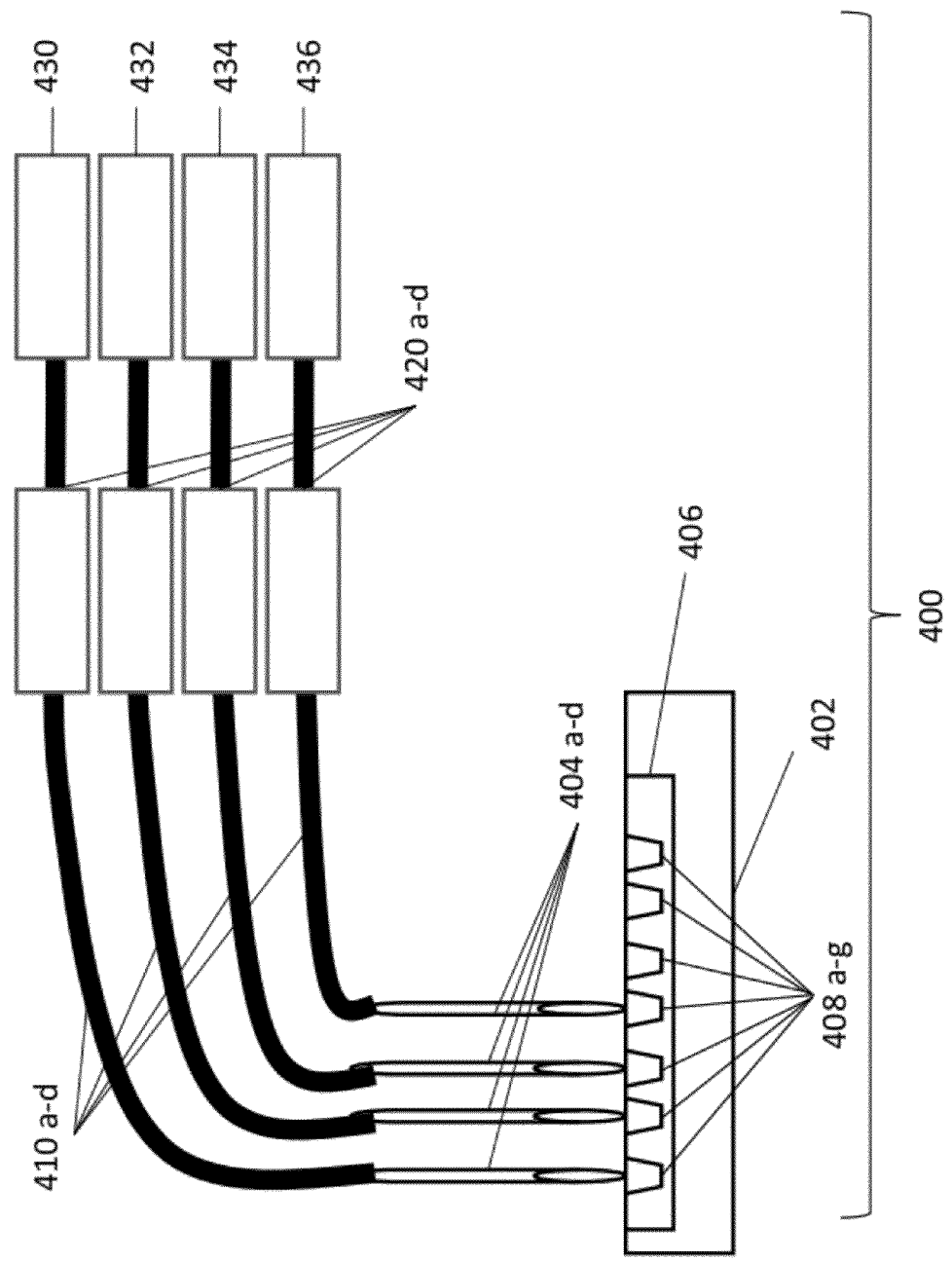
FIG. 4 illustrates a particle analysis apparatus according to another embodiment of the present invention.

FIG. 4 illustrates an alternative embodiment of the multi-sample particle analyzer apparatus 400 of the present invention. Multi-sample particle analyzer apparatus 400 preferably comprises conventional XYZ stage 402 on which is positioned a well plate 406. The plurality of hollow probes 404a-d are stationary as stage 402 moves back and forth (left and right in FIG. 4) and side to side (into and out of the plane of FIG. 4), the stage 402 raises and lower the well plate 406 to a plurality of probes 404a-d so that individual samples from individual source wells 408 are obtained of well plate 406. The probes may be positioned on one or more arms (sometimes referred to herein as a bracket) with each arm independently controlled to coordinate sampling of the sample wells. The arms may be controlled by a computer with instructions for moving the sample well plate and/or the probes.

Once a sample is picked up by one or more of the plurality of probes 404a-d, the sample is moved through a tube 410a-d in communication with the corresponding probe selected from 404a-d such that the tube extends from the respective probe 404a-d into a multi-channel fluid movement device 420 and then into the particle analyzers in communication with the respective tube 210a-d. However, the multi-channel fluid movement device 410a-d may be located after the particle analyzer or before the sample probe. A particle analyzer 430, 432, 434, 436 comprises a flow cell and a laser interrogation device. A laser interrogation device examines individual samples flowing through a flow cell located therein at a laser interrogation point. In between intaking sample material from each of source wells 408, one or more of the plurality of probes 404a-d is allowed to intake a fluid such as air, thereby forming a gas separation between each adjacent sample. The continuous fluid flow stream from each of the probes 404a-d and through the respective tube 410a-d are communicated to a respective individual particle analyzer 430, 432, 434, 436.

Figure 5:
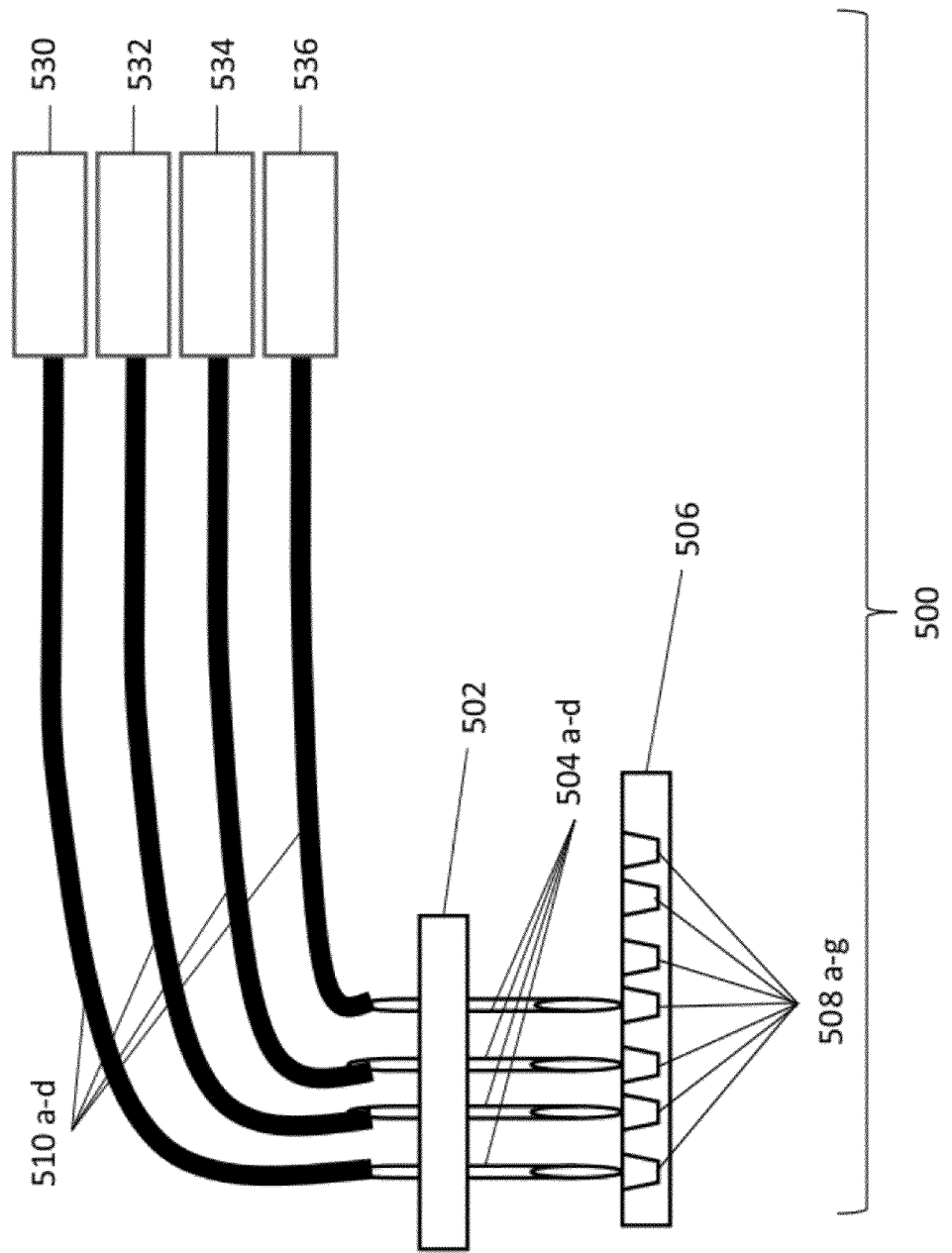
FIG. 5 illustrates a particle analysis apparatus according to another embodiment of the present invention.

FIG. 5 illustrates an alternative embodiment of the multi-sample particle analyzer apparatus 500 of the present invention. Multi-sample particle analyzer apparatus 500 preferably comprises conventional autosampler having adjustable XYZ positioning arm 502 on which is positioned one or more hollow probes 504a-d. As arm 502 moves back and forth (left and right in FIG. 5) and side to side (into and out of the plane of FIG. 5), a plurality of probes selected from 504a-d are lowered into individual source wells 508a-g of well plate 506 to obtain a separate sample for each probe.

Once a portion of a sample is withdrawn from a sample well by one or more of the plurality of probes 504a-d, the sample is moved through a conduit such as a tube 510a-d in communication with the corresponding probe selected from 504a-d such that the tube extends from autosampler XYZ arm 502 and into the particle analyzers in communication with the respective tube 510a-d. The particle analyzer 530, 532, 534, 536 may comprise a flow cell and a laser interrogation device. A laser interrogation device examines individual samples flowing past a laser interrogation point within the particle analyzer. In between intaking sample material from each of source wells 508, one or more of the plurality of probes 504a-d is allowed to intake a fluid such as air, thereby forming a gas separation between each adjacent sample. The continuous fluid flow stream from each of the probes 504a-d and through the respective tube 510a-d are communicated to a respective individual particle analyzer 530, 532, 534, 536.

Figure 6:
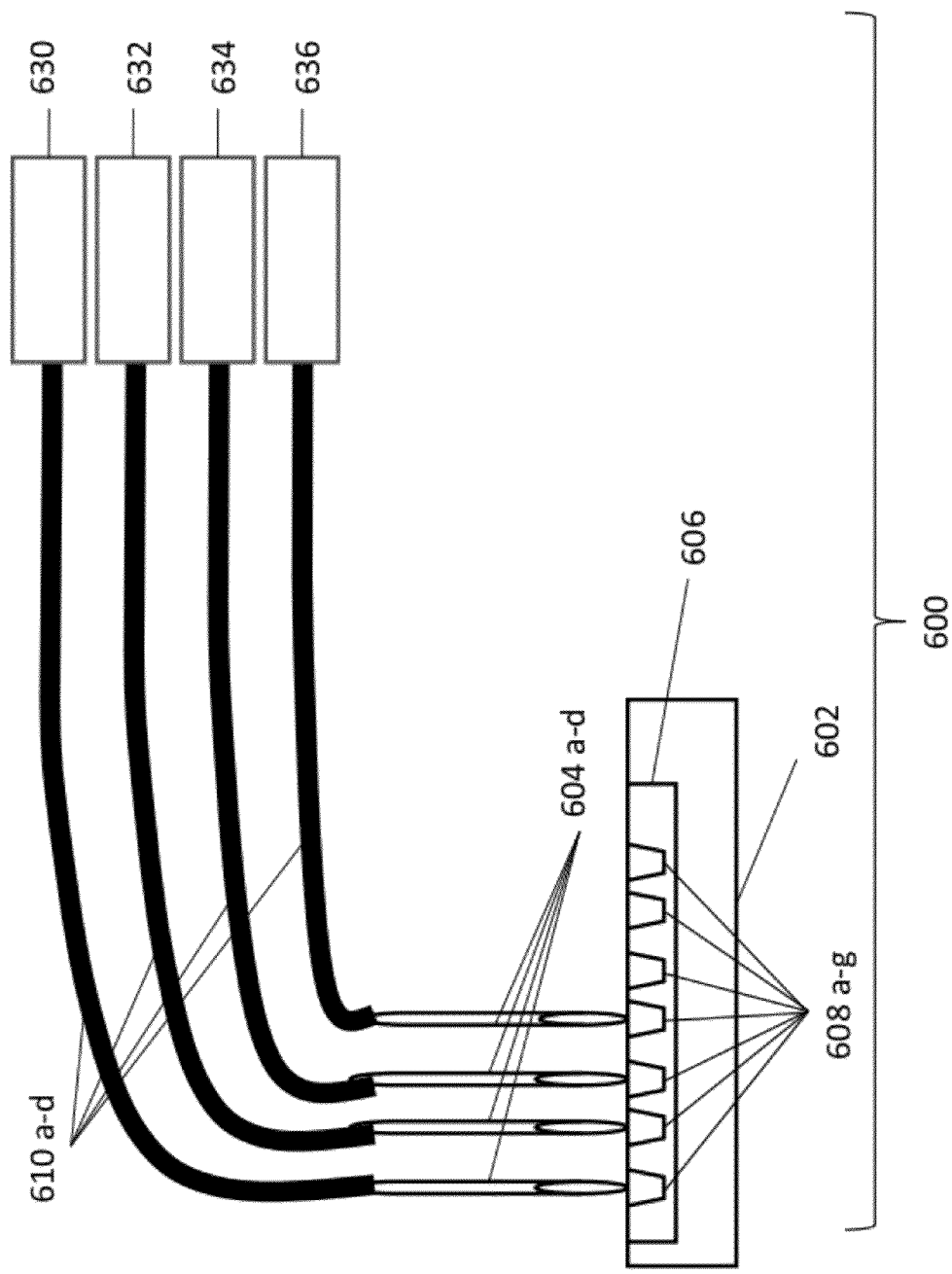
FIG. 6 illustrates a particle analysis apparatus according to another embodiment of the present invention.

FIG. 6 illustrates an alternative embodiment of the multi-sample particle analyzer apparatus 600 of the present invention. Multi-sample particle analyzer apparatus 600 preferably comprises conventional XYZ stage 602 on which is positioned a well plate 606. The plurality of hollow probes 604a-d are stationary as stage 602 moves back and forth (left and right in FIG. 6) and side to side (into and out of the plane of FIG. 6), the stage 602 raises and lower the well plate 606 to a plurality of probes 604a-d so that individual samples from individual source wells 608 are obtained from well plate 606. Probes 604a-d may be fixed in space relative to each other or may move relative to the stage 602 and relative to the other probes 604a-d.

Once a sample is picked up by one or more of the plurality of probes 604a-d, the sample is moved through a tube 610a-d in communication with the corresponding probe selected from 604a-d such that the tube extends from the respective probe 604a-d to the particle analyzer to deliver the sample for analysis. A particle analyzer 630, 632, 634, 636 may comprise a flow cell and a laser interrogation device. A laser interrogation device examines individual samples flowing within the particle analyzer by focusing a beam of light at a laser interrogation point and detecting the beam of laser light or alterations at an optical detector. In between intaking sample material from each of source wells 608, one or more of the plurality of probes 604a-d is allowed to intake a fluid such as air, thereby forming a gas separation between each adjacent sample. The continuous fluid flow stream from each of the probes 604a-d and through the respective tube 610a-d are communicated to a respective individual particle analyzer 630, 632, 634, 636.

Figure 7:
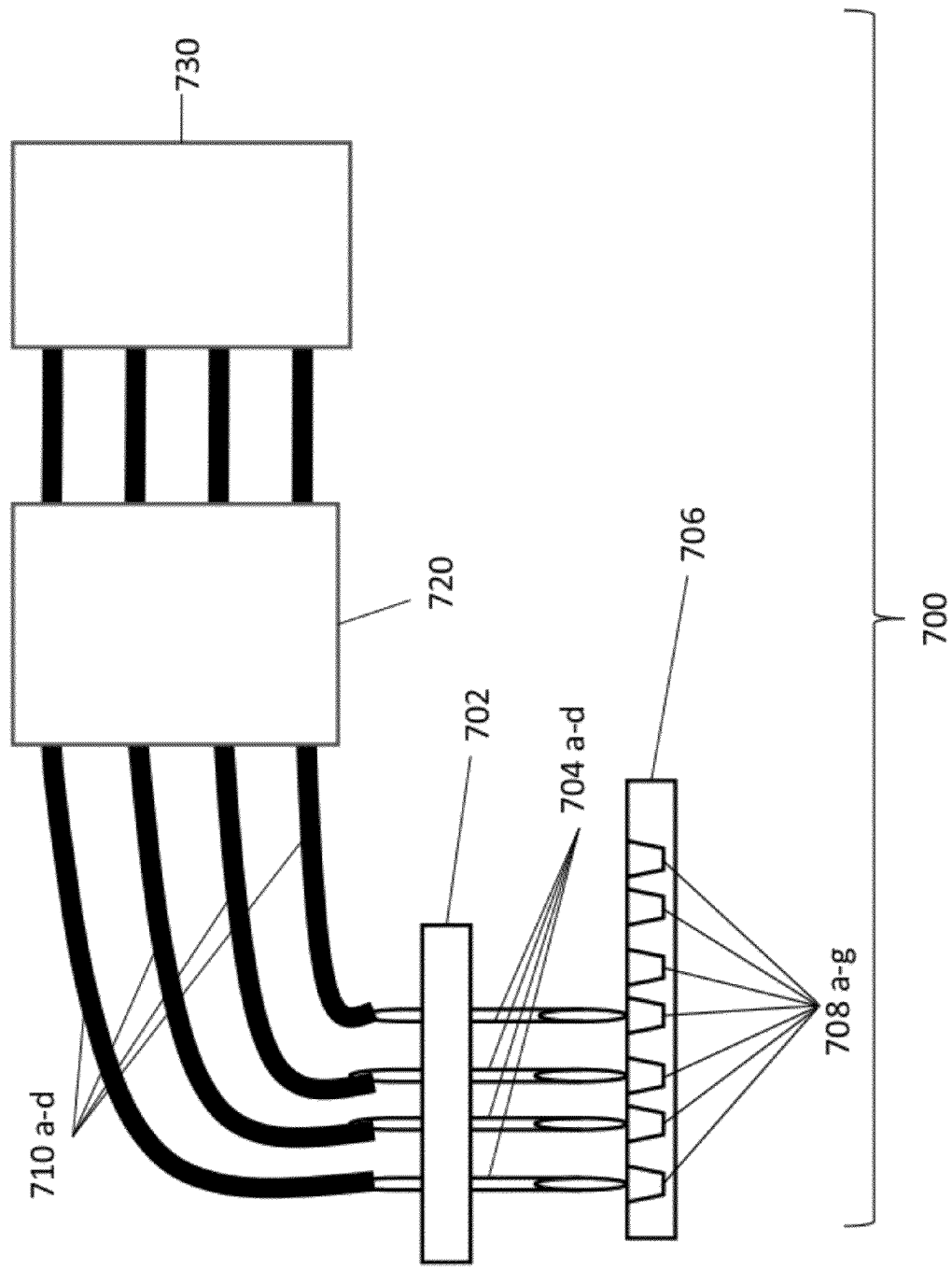
FIG. 7 illustrates a particle analysis apparatus according to another embodiment of the present invention.

FIG. 7 illustrates an alternative embodiment of the multi-sample particle analyzer apparatus 700 of the present invention. Multi-sample particle analyzer apparatus 700 preferably comprises conventional autosampler having adjustable XYZ positioning arm 702 on which is positioned a plurality of hollow probes 704a-d. As arm 702 moves back and forth (left and right in FIG. 7) and side to side (into and out of the plane of FIG. 7), a plurality of probes selected from 704a-d are lowered into individual source wells 708 of well plate 706 to obtain a sample.

Once a sample is picked up by one or more of the plurality of probes 704a-d, the sample is moved through a tube 710a-d in communication with the corresponding probe selected from 704a-d such that the tube extends from autosampler XYZ arm 702 and into a multi-channel fluid movement device 720 and then into the particle analyzer in communication with the respective tube 710a-d. However, the fluid movement device may be located after the particle analyzer 730 or before the probes. A plurality of samples are communicated to a single multi-channel particle analyzer 730 which will multiplex the samples to a single laser interrogation device and analyze the samples simultaneously. A laser interrogation device examines individual samples flowing through a flow cell located within the particle analyzer at a laser interrogation point. In between uptaking sample material from each of source wells 708, one or more of the plurality of probes 704a-d is allowed to uptake a fluid such as air, thereby forming a gas separation between each adjacent sample. The continuous fluid flow stream from each of the probes 704a-d and through the respective tube 710a-d are communicated to a multi-channel particle analyzer 730.

Figure 8:
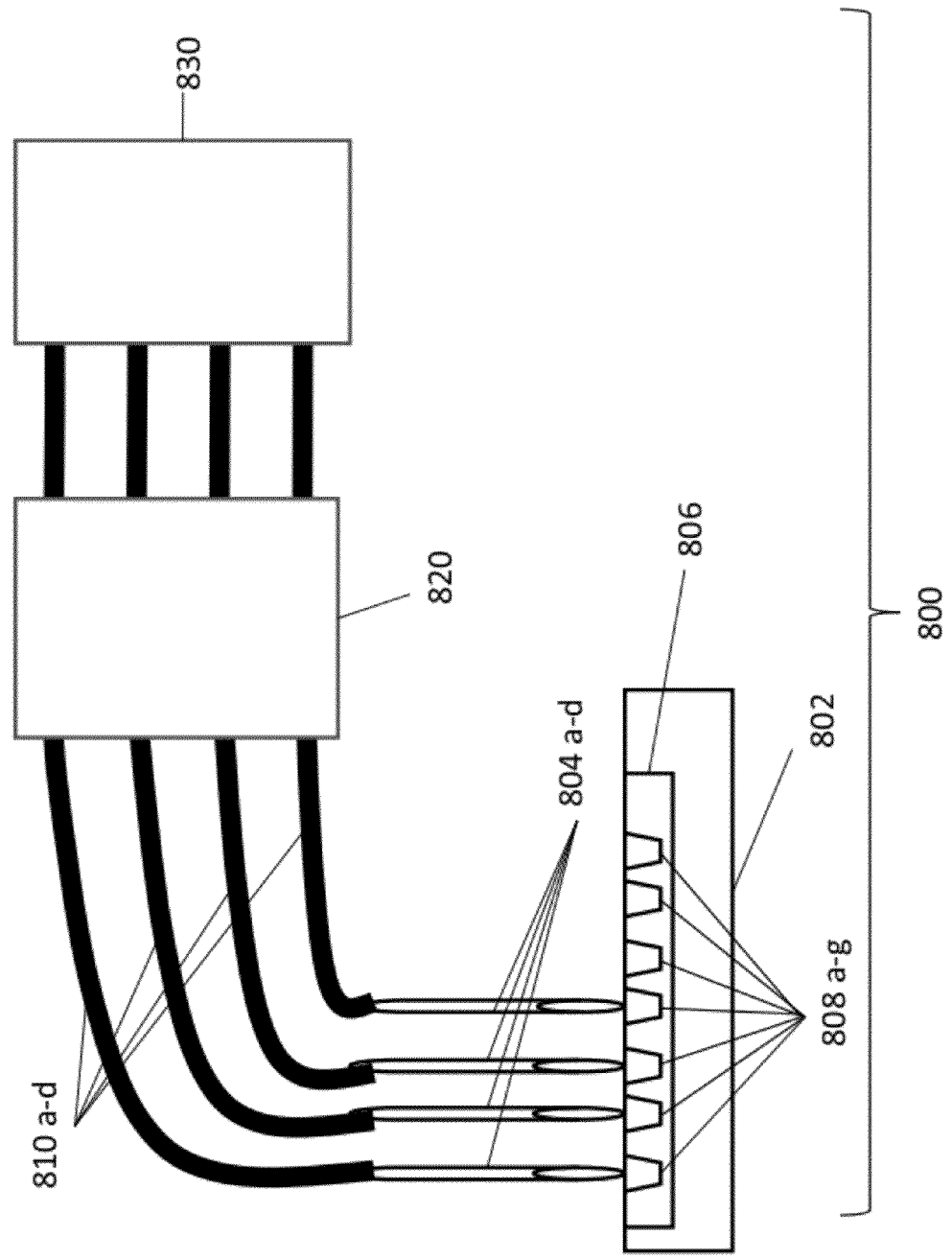
FIG. 8 illustrates a particle analysis apparatus according to another embodiment of the present invention.

FIG. 8 illustrates an alternative embodiment of the multi-sample particle analyzer apparatus 800 of the present invention. Multi-sample particle analyzer apparatus 800 preferably comprises conventional XYZ stage 802 on which is positioned a well plate 806. A plurality of probes 804a-d are stationary as stage 802 moves back and forth (left and right in FIG. 8) and side to side (into and out of the plane of FIG. 8), the stage 802 raises and lower the well plate 806 to the plurality of probes 804a-d so that individual samples from individual source wells 808 of well plate 806 are sampled. The plurality of probes have an open first end and an open second end apposite the first end. The open second end connects to a conduit. The sample flows from the sample well to the particle analyzer through the conduit. A conduit as used herein may be a channel, a tube, a groove or other structure that guides the fluid sample stream or fluid flow path to the particle analyzer.

Once a sample is picked up by one or more of the plurality of probes 804a-d, the sample is moved through a conduit 810a-d in communication with the corresponding probe selected from 804a-d such that the conduit extends from the respective probe 804a-d into a multi-channel fluid movement device 820 and then into the particle analyzers in communication with the respective conduit 810a-d. However, the multiple single-channel fluid movement devices 920a-d may be positioned after the particle analyzer or before the probes. The plurality of samples are communicated to a single multi-channel particle analyzer 830 which will multiplex the samples to a single laser interrogation device and analyze the samples simultaneously. In between uptaking sample material from each of source wells 808, one or more of the plurality of probes 804a-d is allowed to intake a fluid such as air, thereby forming a gas separation between each adjacent sample. The continuous fluid flow stream from each of the probes 804a-d and through the respective tube 810a-d are communicated to a multi-channel particle analyzer 830.

Figure 9:
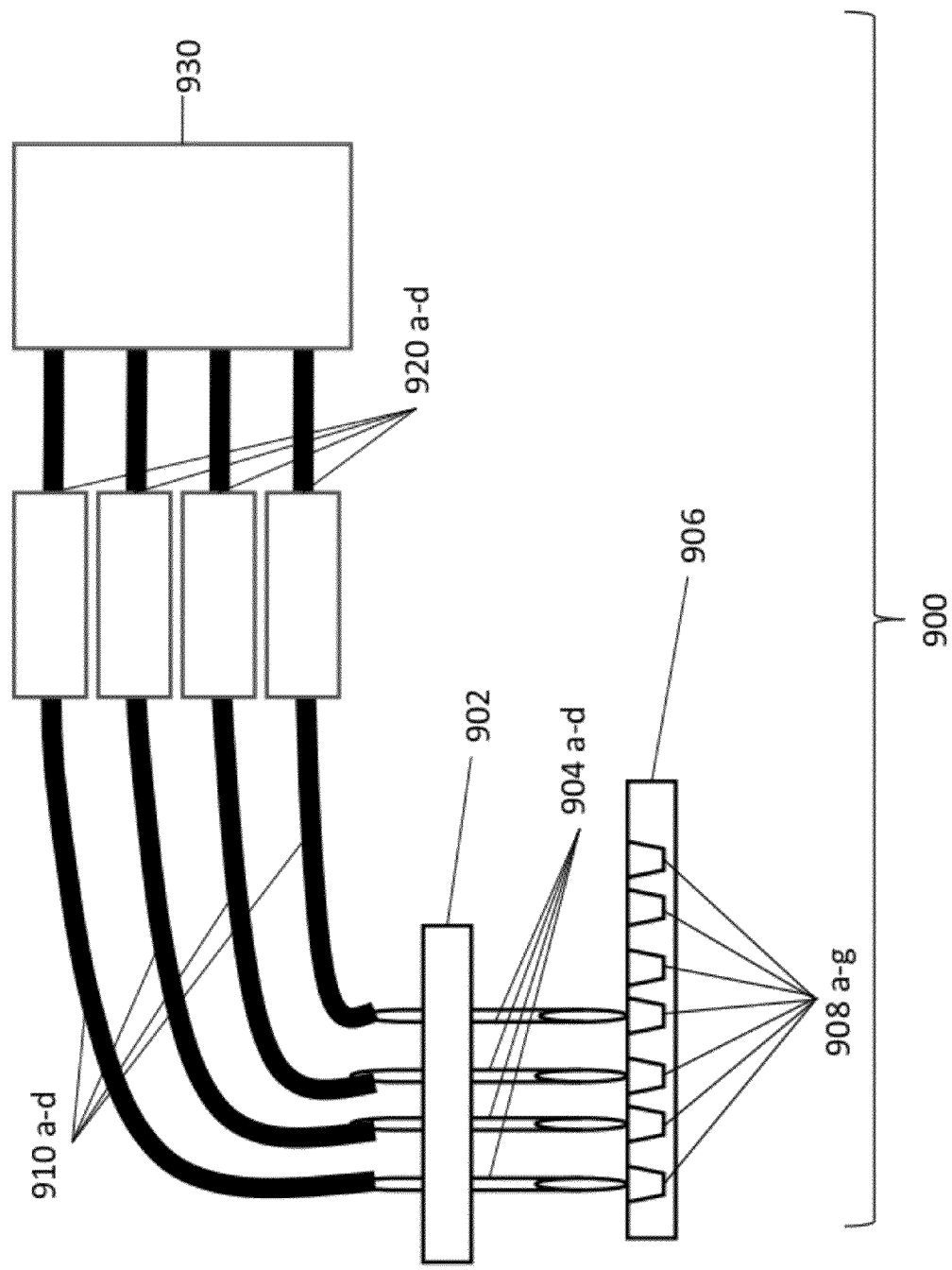
FIG. 9 illustrates a particle analysis apparatus according to another embodiment of the present invention.

FIG. 9 illustrates an alternative embodiment of the multi-sample particle analyzer apparatus 900 of the present invention. Multi-sample article analyzer apparatus 900 preferably comprises conventional autosampler having adjustable XYZ positioning arm 902 on which is positioned a plurality of hollow probes 904a-d. As arm 902 moves back and forth (left and right in FIG. 9) and side to side (into and out of the plane of FIG. 9), a plurality of probes selected from 904a-d are lowered into individual source wells 908 of well plate 906 to obtain a sample.

Once a sample is picked up by one or more of the plurality of probes 904a-d, the sample is moved through a tube 910a-d in communication with the corresponding probe selected from 904a-d such that the tube extends from autosampler XYZ arm 902 and into multiple single-channel fluid movement devices 920a-d and then into the particle analyzers in communication with the respective tube 910a-d. However, the multiple single-channel fluid movement devices 920a-d may be position after the particle analyzer or before the probes. The fluid flow streams may be moved at different rates or the same rates by the fluid movement device. A plurality of samples are communicated to a single multi-channel particle analyzer 930 which will multiplex the samples to a single laser interrogation device and analyze the samples simultaneously. A laser interrogation device examines individual samples flowing through a flow cell located therein at a laser interrogation point. In between intaking sample material from each of source wells 908, one or more of the plurality of probes 904a-d is allowed to intake a fluid such as air, thereby forming a gas separation between each adjacent sample. The continuous fluid flow stream from each of the probes 904a-d and through the respective tube 910a-d are communicated to a multi-channel particle analyzer 930.

Figure 10:
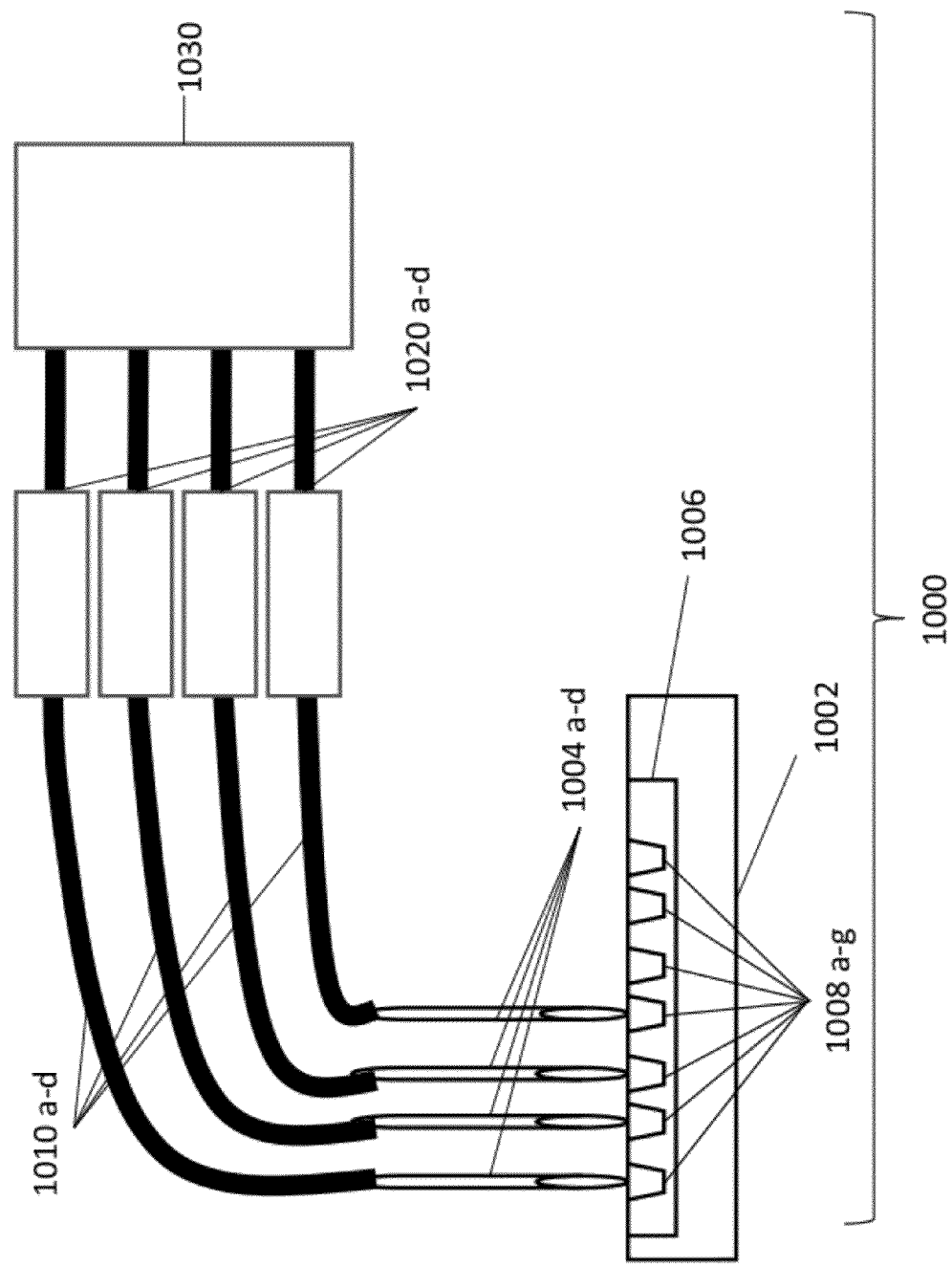
FIG. 10 illustrates a particle analysis apparatus according to another embodiment of the present invention.

FIG. 10 illustrates an alternative embodiment of the multi-sample particle analyzer apparatus 1000 of the present invention. Multi-sample particle analyzer apparatus 1000 preferably comprises conventional XYZ stage 1002 on which is positioned a well plate 1006. The plurality of hollow probes 1004a-d are stationary as stage 1002 moves back and forth (left and right in FIG. 10) and side to side (into and out of the plane of FIG. 10), the stage 1002 raises and lower the well plate 1006 to a plurality of probes 1004a-d so that individual samples from individual source wells 1008 are obtained of well plate 1006.

Once a sample is picked up by one or more of the plurality of probes 1004a-d, the sample is moved through a tube 1010a-d in communication with the corresponding probe selected from 1004a-d such that the tube extends from the respective probe 1004a-d into a multi-channel fluid movement device 1020 and then into the particle analyzers in communication with the respective tube 210a-d. However, the fluid movement device 1020a-d may be located after the particle analyzer 1030. The plurality of samples are communicated to a single multi-channel particle analyzer 1030 which will multiplex the samples to a single laser interrogation device and analyze the samples simultaneously. In between intaking sample material from each of source wells 1008, one or more of the plurality of probes 1004a-d is allowed to intake a fluid such as air, thereby forming a gas separation between each adjacent sample. The continuous fluid flow stream from each of the probes 1004a-d and through the respective tube 1010a-d are communicated to a multi-channel particle analyzer 1030.

Figure 11:
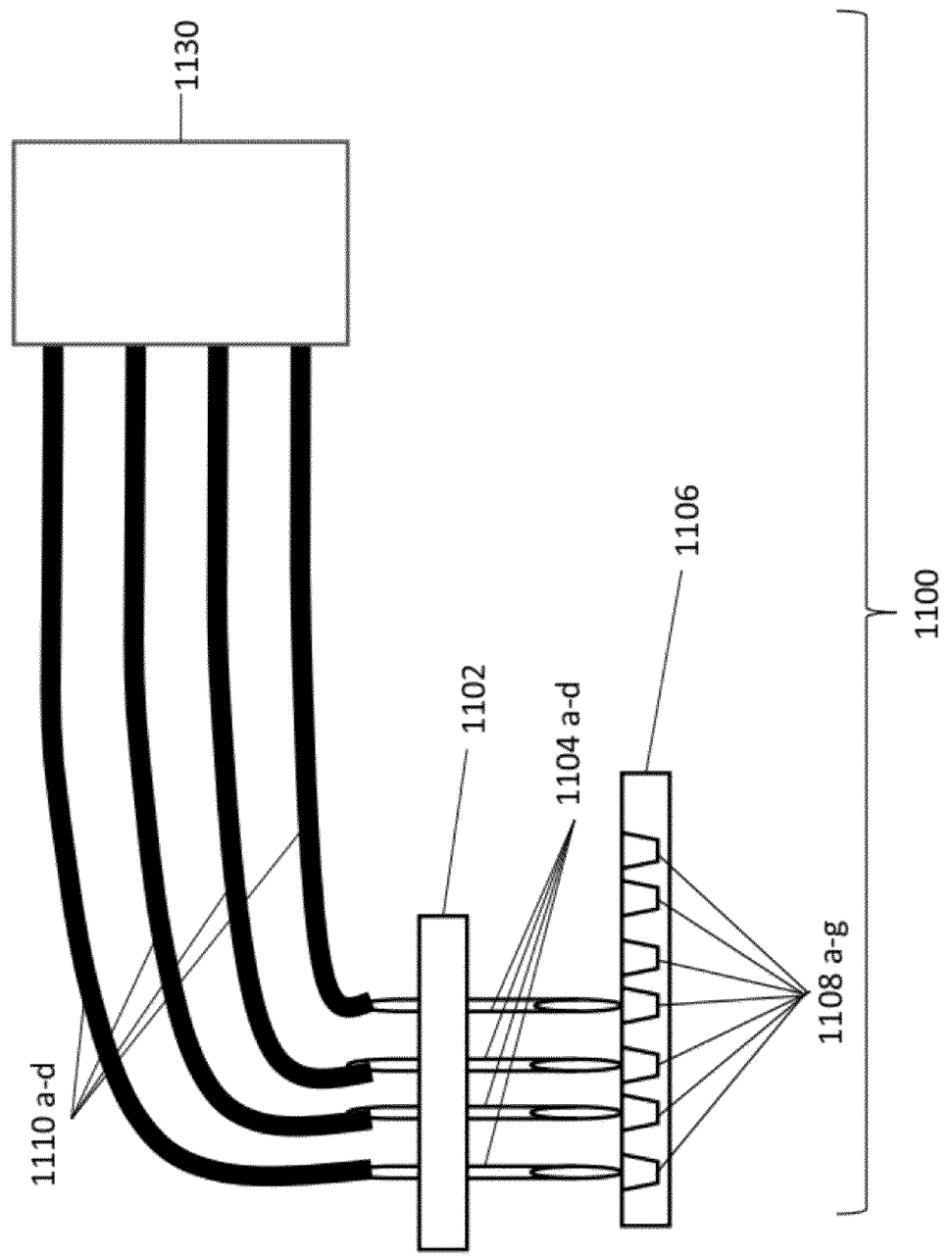
FIG. 11 illustrates a particle analysis apparatus according to another embodiment of the present invention.

FIG. 11 illustrates an alternative embodiment of the multi-sample particle analyzer apparatus 1100 of the present invention. Multi-sample particle analyzer apparatus 1100 preferably comprises an autosampler having adjustable XYZ positioning arm 1102 on which is positioned a plurality of hollow probes 1104a-d. As arm 1102 moves back and forth (left and right in FIG. 11) and side to side (into and out of the plane of FIG. 11), a plurality of probes selected from 1104a-d are lowered into individual source wells 1108 of well plate 1106 to obtain a sample.

Once a sample is picked up by one or more of the plurality of probes 1104a-d, the sample is moved through a tube 1110a-d in communication with the corresponding probe selected from 1104a-d such that the tube extends from autosampler XYZ arm 1102 and into the particle analyzers in communication with the respective tube 1110a-d. The plurality of samples are communicated to a single multi-channel particle analyzer 1130 which will multiplex the samples to a single laser interrogation device and analyze the samples simultaneously. A laser interrogation device interrogates a sample flowing through a flow cell located therein at a laser interrogation point. In between uptaking individual samples from a second source well 1108a-g, a probe 1104a-d introduces a fluid such as air between a first sample and a second sample, thereby forming a gas separation between the first sample and the second sample to form a continuous fluid flow stream to be analyzed. The continuous fluid flow stream from each of the probes 1104a-d and through the respective tube 1110a-d are communicated to a multi-channel particle analyzer 1130.

Figure 12:
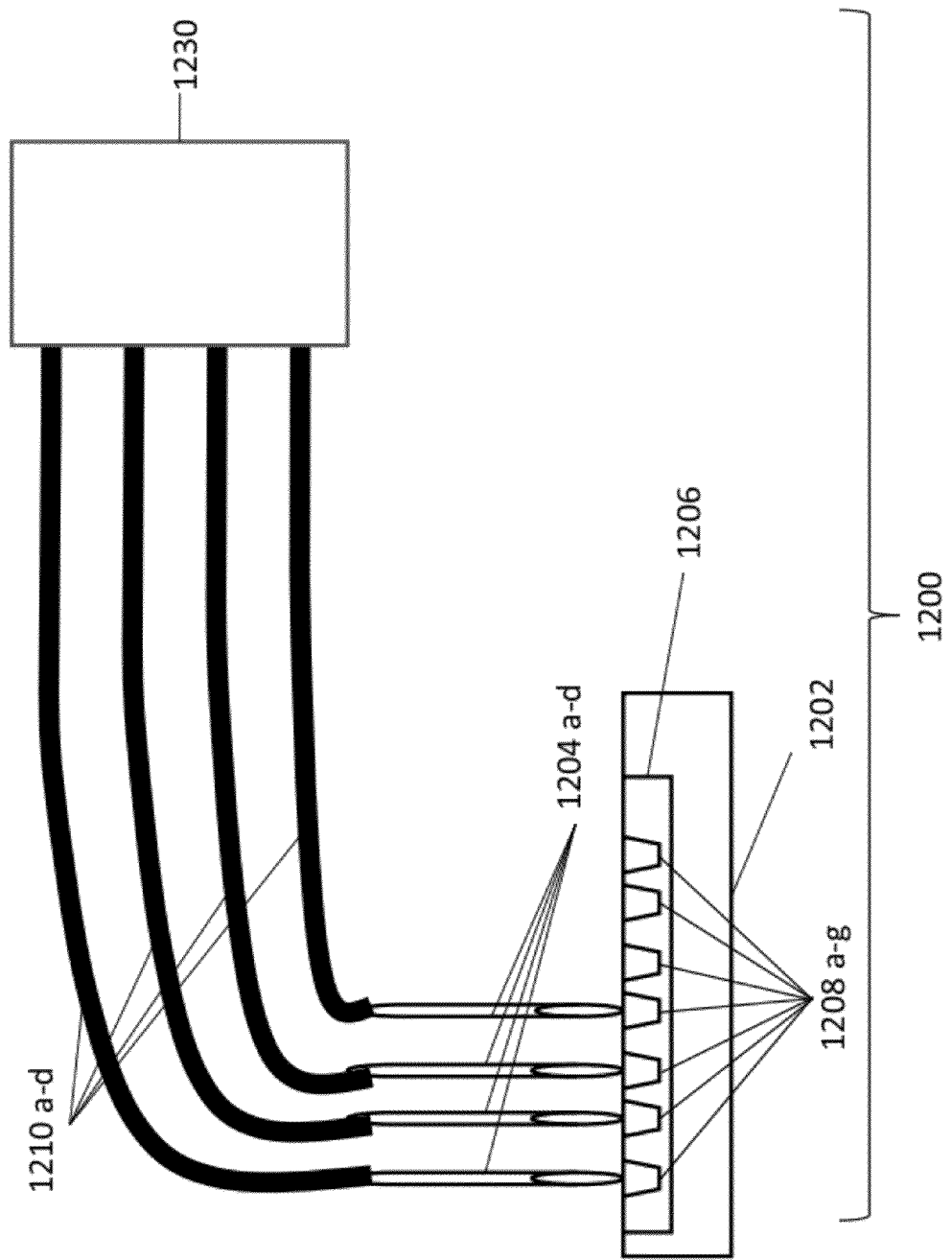
FIG. 12 illustrates a particle analysis apparatus according to another embodiment of the present invention.

FIG. 12 illustrates an alternative embodiment of the multi-sample particle analyzer apparatus 1200 of the present invention. Multi-sample particle analyzer apparatus 1200 preferably comprises conventional XYZ stage 1202 on which is positioned a well plate 1206. The plurality of hollow probes 1204a-d are stationary as stage 1202 moves back and forth (left and right in FIG. 12) and side to side (into and out of the plane of FIG. 12), the stage 1202 raises and lower the well plate 1206 to a plurality of probes 1204a-d so that individual samples from individual source wells 1208 are obtained of well plate 1206.

Once a sample is withdrawn by one or more of the plurality of probes 1204a-d, the sample is moved through a tube 1210a-d in communication with the corresponding probe selected from 1204a-d such that the tube extends from the respective probe 1204a-d into the particle analyzers in communication with the respective tube 1210a-d. The plurality of samples are communicated to a single multi-channel particle analyzer 1230 which will multiplex the samples to a single laser interrogation device and analyze the samples simultaneously. A laser interrogation device examines individual samples flowing through a flow cell located therein at a laser interrogation point. In between intaking sample material from each of source wells 1208, one or more of the plurality of probes 1204a-d is allowed to intake a fluid such as air, thereby forming a gas separation between each adjacent sample. The continuous fluid flow stream from each of the probes 1204a-d and through the respective tube 1210a-d are communicated to a multi-channel particle analyzer 1230.

Figure 13:
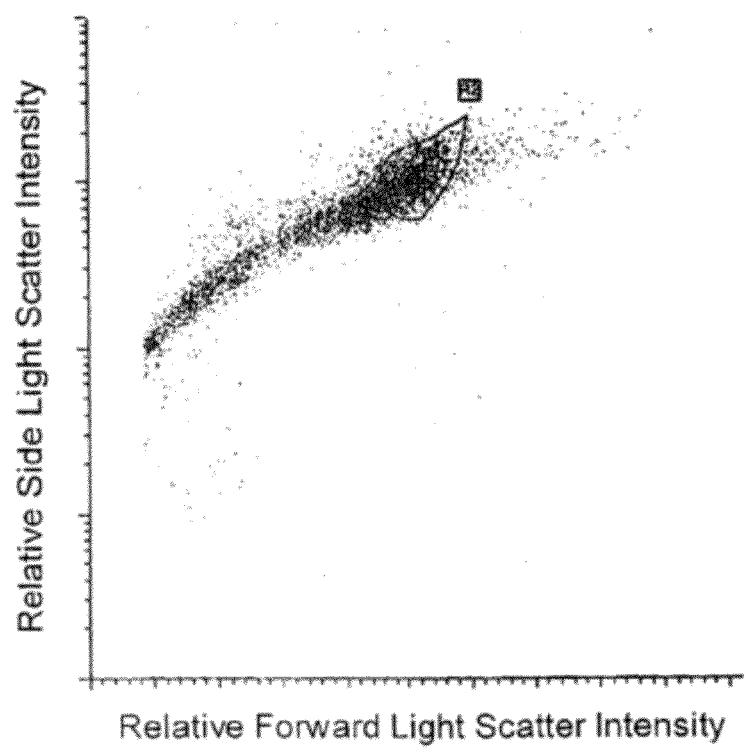
FIG. 13 illustrates cytometry results of forward scatter vs. side scatter with a system and method according to one embodiment of the present invention.

FIG. 13 illustrates cytometry results of forward scatter vs. side scatter with a gate around the particles aligned in the laser beam according to one embodiment of the present invention.

FIG. 14 illustrates flow cytometry results using a fluid means to move samples 1402, 1406, 1410, and 1414 naming particles having a first fluorochrome as a fluorescence tag and four samples 1404, 1408, 1412, and 1416 having particles having a second fluorochrome as a fluorescence tag. FIG. 14 is a graph of Fluorescence vs. Time (1024 channels=60 seconds).

FIG. 15 illustrates an embodiment of the present invention wherein multiple sample probes 1504a-d are positioned in a plurality of sample source wells 1508a-d from a plurality of plates 1506a-d. The samples withdrawn from the plates by the probes are moved to a particle analyzer (not shown) through conduits 1510a-d connected to a respective probe 1508a-d. The plates may be positioned on a platform that moves the plates in the XYZ dimensions in space or the probes may move in the XYZ dimensions in space relative to the plates, relative to each other or both.

The autosampler of the present invention may be any conventional autosampler suitable for intaking samples from a well plate or other sample source container. For example, an autosampler as produced by TM the Gilson 223 liquid manager.

The XYZ stage of the present invention may be any XYZ stage suitable for positioning a well plate.

The use of automation, for example a robotic plate loader, in plate delivery and retrieval for the autosampler or XYZ stage may allow automation of the overall screening process.

One preferred probe for the present invention is a 0.01 inch ID, inch OD stainless steel needle compatible with HPLC ferrule fittings. Similar probes with reinforced tubular sheaths are suited for multiprobe sampling. The current embodiment of the invention utilizes a Gilson interface module for bidirectional communication between a computer and a probe manipulating arm or XYZ stage, and a fluid movement device. Software designed using commercial languages, such as C++, C#, Java, etc. may be used to control the speed and distance of probe motions in all 3 dimensions, the sensing of probe contact with liquid in a source well to assure reproducible sample volumes, and the speed of the fluid movement device. A computer or other known device may be used to control the autosampler or XYZ stage to regulate sample size and bubble size by varying the time that the probe is in a source well or above a source well. Also, various sample handlers, XYZ stages, and sampler handling systems that may be useful in the apparatus and method of the present invention are well known in the art.

In order to reduce sample carryover a rinsing station or device that may be attached to the autosampler to rinse the autosampler probe between intakes of sample and/or buffer solution. The rinsing fluid may be water, a mild detergent, or a solvent, such as a solvent in which each of the particles in one or more of the samples is dissolved. When the particles are merely suspended in a suspension fluid, the rinsing fluid may be the same as the suspension fluid.

Various conventional means may be employed to move the sample through the system. For example, peristaltic pumps or injection devices may be used with a particle analyzer such as a flow cytometer or an acoustic cytometry apparatus for the present invention. According to one embodiment, the peristaltic pump is a multi channel or head pump that accommodates up to 4 separate sample tubes leading to particle analyzers.

There are various types of tubing may be used for the fluid flow path of the present invention, as long as the tubing may function as high speed multi-sample tubing. When thin walled PVC (polyvinyl chloride) tubing is used as the tubing for the present invention, carryover between samples is substantially reduced compared to conventional peristaltic tubing.

Various types of flow cytometers may be used with the present invention. Commercially available flow cytometers from Becton Dickinson (FACSCAlibur, FACSArray, FACSCantoII and LSRII), Beckman Coulter (CyAn) and Accuri Cytometers (C6) have all been proven compatible with embodiments of the current invention. The use of the real-time software in conjunction with flow cytometer controlling software may allow the samples from a given source well to be rapidly re-checked during sampling and data analysis to prove that "hits" from neighboring source wells do not arise from cross-contamination, or to identify hits for additional treatment or testing.

On-line data analysis may be used in the flow cytometer to compare data between well plates and facilitate overall utility of the data in conjunction with automation. Operation of the flow cytometer at higher pressure generally increases the sample flow rate and may, in some circumstances yield a higher throughput. Also, operation of the flow cytometer with increased time resolution in data software may allow resolution of samples at higher throughput rates.

Both peristaltic pumps and air bubbles have been used in a variety of detection devices with flowing samples. For example, bubbles are commonly used in clinical instruments to separate samples and the peristaltic pumps to move fluids. However, in flow cytometry there is specific teaching against air bubbles with the idea that, optimally, the bubbles should be removed from the sample prior to injection into the flow cytometer. However, in the current invention, carefully controlling the air bubble and using a temporal separation of the specimens to eliminate the air bubble from analysis, the introduction of air bubbles between samples has proven to have little or no effect on the quality of results.

Using the flow cytometry apparatus of the present invention, it has already been possible to move and analyze up to 40 samples per minute in a single channel (consisting of a probe, tube, peristaltic pump). In a preferred embodiment, utilizing multiple probes, 80-400 samples can be moved and analyzed per minute.

Among the advantages of the flow cytometer apparatus of the present invention is that it allows rapid sampling of small volumes of sample. For example, a sample drawn into the fluid stream tubing at a rate of about 0.3 ul/sec requires less than a 2 ul sample.

The throughput of the flow cytometry apparatus of the present invention tends to be more affected by the behavior of the autosampler rather than the characteristics of the fluid movement device, the tubing or the flow cytometer. Thus, to the extent that an autosampler can move more rapidly from source well to source well, higher throughputs are achieved. Improved accuracy in volume intake/delivery by the autosampler leads to smaller sample volumes and improved throughputs.

In another embodiment of the present invention, a plurality of samples are simultaneously picked up using a multichannel autosampler comprising a plurality of sampling probes and a plurality of sample delivery tubes. In this embodiment, a peristaltic pump or other sample moving device moves the plurality of samples in the delivery tubes through the pump simultaneously using a plurality of pump heads or injection devices thus providing a plurality of channels. By having a plurality of probes sampling a plurality of wells of a microplate simultaneously, each channel is delivered to a separate input port of a single particle analyzer or separate particle analyzer to enable each channel to be analyzed in parallel, thereby increasing sample throughput 100% for each channel added.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. For example, the arm 102 in FIG. 1 directs the movement of probe 104*a* independent of the movement of probes 104*b*, 104*c* or 104*d*. For embodiments where there are four probes illustrated, the invention is not limited thereto. For example, the invention may include two or more probes each attached to be a conduit leading to a separate particle analyzer or a multi-channel particle analyzer. A means for moving the fluid can be positioned before or after the particle analyzer or before the probes. The entire disclosures of all references, applications, patents, and publications cited above are hereby incorporated by reference.

What is claimed:

1. A method for analyzing a plurality of samples, comprising:
   obtaining with an autosampler a plurality of samples from a first plate having a plurality of sample wells wherein the autosampler comprises a plurality of probes for sampling the plurality of samples and wherein each probe of the plurality of probes is in communication with a separate flow cytometer via a separate conduit;
   moving the plurality of samples comprising particles into a fluid flow stream for each separate conduit;
   separating adjacent ones of the plurality of samples from each other in the fluid flow stream by a separation gas, thereby forming a gas-separated fluid flow stream;
   independently guiding the gas-separated fluid flow stream to and through each separate flow cytometer;
   operating each separate flow cytometer to focus the gas-separated fluid flow stream and to selectively analyze the particles in each of the plurality of samples as the gas-separated fluid flow stream passes through each separate flow cytometer.

2. The method of claim 1 wherein the first plate is positioned on a platform that is moveable in the xyz direction to bring the samples to the probes.

3. The method of claim 1 wherein the step of moving the plurality of samples are moved by a fluid moving device located before or after each separate flow cytometer.

4. The method of claim 1 wherein the fluid moving device is a multihead peristaltic pump.

5. The method of claim 1 wherein the step of moving is selected from the group consisting of moving with gravity, moving with suction, moving with pumping or and moving with pushing via a peristaltic pump.

6. The method of claim 1 wherein the separate conduit is tubing.

7. The method of claim 1 wherein the probes are positionable to the samples on the first plate.

8. The method of claim 1 wherein at least one of the probes of the plurality of probes is positionable to a sample on a second plate.

9. The method of claim 1 wherein the step of moving the plurality of fluid sample streams is at a rate that is independently controlled.

10. A flow cytometry apparatus comprising:
    an autosampler comprising a plurality of probes with each probe suitable for inserting a plurality of samples comprising particles from a plurality of respective source wells into a separate fluid flow stream;
    a plurality of flow cytometers in communication with the plurality of probes of the autosampler via a separate conduit connecting a probe of the plurality of probes with a separate flow cytometer of the plurality of flow cytometers; and
    a fluid movement device for moing the plurality of samples in each separate fluid flow streams through each separate conduit to a selected flow cytometer of the plurality of flow cytometers, the plurality of probes introducing aliquots of a separation fluid between successive ones of the plurality of samples in each of the separate fluid flow stream to configure each of the separate fluid flow streams as a gas-separated fluid flow stream, each of the plurality of flow cytometers focusing the gas-separated fluid flow stream delivered by the separate conduit and selectively analyzing the particles in each of the plurality of samples as the gas-separated fluid flow stream passes through each separate cytometer of the plurality of cytometers.

11. The apparatus of claim 10 wherein the plurality of probes are positioned on an arm.

12. The apparatus of claim 11 wherein the arm is fixed relative to the position of the plate.

13. The apparatus of claim 10 wherein the plurality of probes are positionable relative to the plate.

14. The apparatus of claim 10 wherein the probes are independently positionable relative to each other.

15. The apparatus of claim 10 wherein the fluid movement device is a pump.

16. The apparatus of claim 15 wherein the pump is a peristaltic pump.

17. The apparatus of claim 10 wherein the fluid movement device is positioned before or after a flow cytometer.

18. The apparatus of claim 10 wherein the step of moving is selected from the group consisting of pumping via peristaltic pump, moving with pushing via peristaltic pump, moving with suction or moving with gravity.

19. The apparatus of claim 18 wherein the fluid movement device comprises a plurality of fluid movement devices each associated with the separate conduit.

* * * * *